United States Patent
Kaplan et al.

(10) Patent No.: US 7,481,834 B2
(45) Date of Patent: *Jan. 27, 2009

(54) STENT FOR PLACEMENT AT LUMINAL OS

(75) Inventors: Aaron V. Kaplan, Norwich, VT (US); Jaime Vargas, Redwood City, CA (US)

(73) Assignee: Tryton Medical, Inc., Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/807,643

(22) Filed: Mar. 23, 2004

(65) Prior Publication Data

US 2004/0204754 A1 Oct. 14, 2004

Related U.S. Application Data

(60) Provisional application No. 60/463,075, filed on Apr. 14, 2003.

(51) Int. Cl.
*A61M 29/00* (2006.01)
(52) U.S. Cl. ...................................... 623/1.15
(58) Field of Classification Search ....... 623/1.11–1.54; 606/194
See application file for complete search history.

(56) References Cited

U.S. PATENT DOCUMENTS

| | | | |
|---|---|---|---|
| 4,950,227 A | 8/1990 | Savin et al. | |
| 4,958,634 A | 9/1990 | Jang | |
| 4,994,071 A | 2/1991 | MacGregor | |
| 5,071,406 A | 12/1991 | Jang | |
| 5,074,845 A | 12/1991 | Miraki et al. | |
| 5,102,417 A | 4/1992 | Palmaz | |
| 5,226,889 A * | 7/1993 | Sheiban | 604/103.1 |
| 5,304,132 A | 4/1994 | Jang | |
| 5,342,387 A | 8/1994 | Summers | |
| 5,383,892 A | 1/1995 | Cardon et al. | |
| 5,395,333 A | 3/1995 | Brill | |
| 5,415,635 A | 5/1995 | Bagaoisan et al. | |
| 5,507,769 A | 4/1996 | Marin et al. | |
| 5,522,882 A | 6/1996 | Gaterud et al. | |
| 5,540,712 A * | 7/1996 | Kleshinski et al. | 623/1.19 |

(Continued)

FOREIGN PATENT DOCUMENTS

EP   0712 614 B1   11/1995

(Continued)

OTHER PUBLICATIONS

Marked up figures 5 and 6 of 6,293,964.*

(Continued)

*Primary Examiner*—William H. Matthews
*Assistant Examiner*—Ann Schillinger
(74) *Attorney, Agent, or Firm*—Knobbe, Martens, Olson & Bear, LLP

(57) ABSTRACT

A prosthesis includes a radially expansible scaffold in at least two circumferential anchors extending from the scaffold. The prosthesis is placed across an os between a main body lumen and a branch lumen. The scaffold is expanded within the branch lumen and the circumferential anchors deformed outwardly to conform to the wall of the main body lumen. Optionally, a second prosthesis may be placed within the main body lumen after the first prosthesis has been deployed.

29 Claims, 8 Drawing Sheets

U.S. PATENT DOCUMENTS

| | | | |
|---|---|---|---|
| 5,575,817 A | 11/1996 | Martin | |
| 5,593,442 A | 1/1997 | Klein | |
| 5,607,444 A * | 3/1997 | Lam | 606/194 |
| 5,609,605 A | 3/1997 | Marshall et al. | |
| 5,609,627 A | 3/1997 | Goicoechea et al. | |
| 5,613,980 A | 3/1997 | Chauhan | |
| 5,632,762 A | 5/1997 | Myler | |
| 5,645,560 A | 7/1997 | Crocker et al. | |
| 5,656,036 A | 8/1997 | Palmaz | |
| 5,658,251 A | 8/1997 | Ressemann et al. | |
| 5,662,608 A | 9/1997 | Imran et al. | |
| 5,669,924 A | 9/1997 | Shaknovich | |
| 5,669,932 A | 9/1997 | Fischell et al. | |
| 5,713,917 A | 2/1998 | Leonhardt et al. | |
| 5,718,712 A | 2/1998 | Bonnal et al. | |
| 5,720,724 A | 2/1998 | Ressemann et al. | |
| 5,720,735 A | 2/1998 | Dorros | |
| 5,741,325 A | 4/1998 | Chaikof et al. | |
| 5,749,825 A | 5/1998 | Fischell et al. | |
| 5,749,851 A | 5/1998 | Wang | |
| 5,749,890 A * | 5/1998 | Shaknovich | 606/198 |
| 5,755,734 A | 5/1998 | Richter et al. | |
| 5,755,735 A | 5/1998 | Richter et al. | |
| 5,755,771 A * | 5/1998 | Penn et al. | 623/1.15 |
| 5,788,708 A | 8/1998 | Hegde et al. | |
| 5,810,871 A | 9/1998 | Tuckey et al. | |
| 5,824,052 A | 10/1998 | Khosravi et al. | |
| 5,827,320 A | 10/1998 | Richter et al. | |
| 5,843,116 A | 12/1998 | Crocker et al. | |
| 5,855,598 A | 1/1999 | Pinchuk | |
| 5,860,998 A | 1/1999 | Robinson et al. | |
| 5,868,777 A * | 2/1999 | Lam | 606/194 |
| 5,868,783 A | 2/1999 | Tower | |
| 5,893,887 A | 4/1999 | Jayaraman | |
| 5,897,588 A | 4/1999 | Hull et al. | |
| 5,906,640 A | 5/1999 | Penn et al. | |
| 5,906,641 A | 5/1999 | Thompson et al. | |
| 5,922,019 A * | 7/1999 | Hankh et al. | 623/1.13 |
| 5,961,546 A | 10/1999 | Robinson et al. | |
| 5,964,771 A * | 10/1999 | Beyar et al. | 606/108 |
| 5,967,971 A | 10/1999 | Bolser | |
| 5,980,532 A | 11/1999 | Wang | |
| 6,004,347 A | 12/1999 | McNamara et al. | |
| 6,017,363 A | 1/2000 | Hojeibane | |
| 6,027,486 A | 2/2000 | Crocker et al. | |
| 6,027,517 A | 2/2000 | Crocker et al. | |
| 6,033,434 A | 3/2000 | Borghi | |
| 6,033,435 A * | 3/2000 | Penn et al. | 623/1.15 |
| 6,048,361 A | 4/2000 | Von Oepen | |
| 6,051,020 A | 4/2000 | Goicoechea et al. | |
| 6,053,913 A | 4/2000 | Tu et al. | |
| 6,053,941 A | 4/2000 | Lindenberg et al. | |
| 6,056,775 A * | 5/2000 | Borghi et al. | 623/1.16 |
| 6,056,776 A | 5/2000 | Lau et al. | |
| 6,066,155 A | 5/2000 | Amann et al. | |
| 6,066,168 A | 5/2000 | Lau et al. | |
| 6,068,654 A | 5/2000 | Berg et al. | |
| 6,068,655 A | 5/2000 | Sequin et al. | |
| 6,077,297 A | 6/2000 | Robinson et al. | |
| 6,090,127 A * | 7/2000 | Globerman | 606/194 |
| 6,090,133 A | 7/2000 | Richter et al. | |
| 6,096,071 A * | 8/2000 | Yadav | 623/1.15 |
| 6,096,073 A | 8/2000 | Webster et al. | |
| 6,099,497 A | 8/2000 | Adams et al. | |
| 6,099,560 A | 8/2000 | Penn et al. | |
| 6,120,523 A | 9/2000 | Crocker et al. | |
| 6,127,597 A * | 10/2000 | Beyar et al. | 606/86 |
| 6,129,738 A | 10/2000 | Lashinski et al. | |
| 6,156,052 A | 12/2000 | Richter et al. | |
| 6,159,238 A | 12/2000 | Killion et al. | |
| 6,162,243 A | 12/2000 | Gray et al. | |
| 6,165,195 A | 12/2000 | Wilson et al. | |
| 6,168,617 B1 | 1/2001 | Blaeser et al. | |
| 6,183,509 B1 | 2/2001 | Dibie | |
| 6,206,910 B1 | 3/2001 | Berry et al. | |
| 6,210,429 B1 | 4/2001 | Vardi et al. | |
| 6,214,036 B1 * | 4/2001 | Letendre et al. | 623/1.11 |
| 6,221,080 B1 | 4/2001 | Power | |
| 6,221,096 B1 * | 4/2001 | Aiba et al. | 623/1.11 |
| 6,221,098 B1 | 4/2001 | Wilson et al. | |
| 6,231,543 B1 | 5/2001 | Hegde et al. | |
| 6,241,738 B1 * | 6/2001 | Dereume | 606/108 |
| 6,241,744 B1 * | 6/2001 | Imran et al. | 606/159 |
| 6,254,593 B1 | 7/2001 | Wilson | |
| 6,258,116 B1 | 7/2001 | Hojeibane | |
| 6,261,305 B1 | 7/2001 | Marotta et al. | |
| 6,261,316 B1 | 7/2001 | Shaolian et al. | |
| 6,264,682 B1 | 7/2001 | Wilson et al. | |
| 6,264,686 B1 | 7/2001 | Rieu et al. | |
| 6,267,783 B1 | 7/2001 | Letendre et al. | |
| 6,270,525 B1 | 8/2001 | Letendre et al. | |
| 6,280,412 B1 | 8/2001 | Pederson, Jr. et al. | |
| 6,287,315 B1 | 9/2001 | Wijeratne et al. | |
| 6,287,336 B1 * | 9/2001 | Globerman et al. | 623/1.3 |
| 6,290,728 B1 * | 9/2001 | Phelps et al. | 623/23.7 |
| 6,293,964 B1 | 9/2001 | Yadav | |
| 6,325,826 B1 | 12/2001 | Vardi et al. | |
| 6,331,186 B1 | 12/2001 | Wang et al. | |
| 6,344,052 B1 | 2/2002 | Greenan et al. | |
| 6,346,089 B1 | 2/2002 | Dibie | |
| 6,352,551 B1 | 3/2002 | Wang | |
| 6,361,544 B1 | 3/2002 | Wilson et al. | |
| 6,383,212 B2 | 5/2002 | Durcan et al. | |
| 6,383,213 B2 | 5/2002 | Wilson et al. | |
| 6,387,120 B2 | 5/2002 | Wilson et al. | |
| 6,391,032 B2 | 5/2002 | Blaeser et al. | |
| 6,395,008 B1 | 5/2002 | Ellis et al. | |
| 6,402,778 B2 | 6/2002 | Wang | |
| 6,409,741 B1 | 6/2002 | Crocker et al. | |
| 6,409,750 B1 | 6/2002 | Hyodoh et al. | |
| 6,409,755 B1 | 6/2002 | Vrba | |
| 6,409,757 B1 | 6/2002 | Trout, III et al. | |
| 6,428,567 B2 | 8/2002 | Wilson et al. | |
| 6,436,104 B2 | 8/2002 | Hojeibane | |
| 6,436,134 B2 | 8/2002 | Richter et al. | |
| 6,440,165 B1 | 8/2002 | Richter et al. | |
| 6,451,050 B1 | 9/2002 | Rudakov et al. | |
| 6,478,814 B2 | 11/2002 | Wang et al. | |
| 6,482,211 B1 | 11/2002 | Choi | |
| 6,482,227 B1 * | 11/2002 | Solovay | 623/1.13 |
| 6,488,700 B2 | 12/2002 | Klumb et al. | |
| 6,508,836 B2 | 1/2003 | Wilson et al. | |
| 6,517,558 B2 | 2/2003 | Gittings et al. | |
| 6,524,335 B1 * | 2/2003 | Hartley et al. | 623/1.13 |
| 6,540,779 B2 | 4/2003 | Richter et al. | |
| 6,547,813 B2 | 4/2003 | Stiger et al. | |
| 6,554,856 B1 * | 4/2003 | Doorly et al. | 623/1.15 |
| 6,562,061 B1 | 5/2003 | Wang et al. | |
| 6,565,597 B1 * | 5/2003 | Fearnot et al. | 623/1.14 |
| 6,572,649 B2 | 6/2003 | Berry et al. | |
| 6,579,312 B2 | 6/2003 | Wilson et al. | |
| 6,579,314 B1 | 6/2003 | Lombardi et al. | |
| 6,582,394 B1 | 6/2003 | Reiss et al. | |
| 6,589,274 B2 * | 7/2003 | Stiger et al. | 623/1.11 |
| 6,596,020 B2 | 7/2003 | Vardi et al. | |
| 6,599,316 B2 | 7/2003 | Vardi et al. | |
| 6,607,552 B1 | 8/2003 | Hanson | |
| 6,626,934 B2 | 9/2003 | Blaeser et al. | |
| 6,637,107 B2 | 10/2003 | Yasuhara et al. | |
| 6,652,580 B1 * | 11/2003 | Chuter et al. | 623/1.36 |
| 6,656,215 B1 | 12/2003 | Yanez et al. | |
| 6,656,216 B1 | 12/2003 | Hossainy et al. | |
| 6,663,665 B2 | 12/2003 | Shaolian et al. | |
| 6,663,666 B1 | 12/2003 | Quiachon et al. | |

| | | |
|---|---|---|
| 6,673,104 B2 | 1/2004 | Barry |
| 6,673,106 B2 | 1/2004 | Mitelberg et al. |
| 6,673,107 B1* | 1/2004 | Brandt et al. ............... 623/1.35 |
| 6,682,557 B1 | 1/2004 | Quiachon et al. |
| 6,706,062 B2 | 3/2004 | Vardi et al. |
| 6,726,714 B2 | 4/2004 | DiCaprio et al. |
| 6,740,113 B2* | 5/2004 | Vrba ........................ 623/1.12 |
| 6,756,094 B1 | 6/2004 | Wang |
| 6,764,504 B2 | 7/2004 | Wang |
| 6,770,092 B2* | 8/2004 | Richter ...................... 623/1.35 |
| 6,790,224 B2 | 9/2004 | Gerberding |
| 6,805,697 B1 | 10/2004 | Helm et al. |
| 6,805,702 B1 | 10/2004 | Chen et al. |
| 6,824,553 B1 | 11/2004 | Samson et al. |
| 6,830,575 B2 | 12/2004 | Stenzel et al. |
| 6,843,802 B1 | 1/2005 | Villalobos et al. |
| 6,852,116 B2 | 2/2005 | Leonhardt et al. |
| 6,872,215 B2 | 3/2005 | Crocker et al. |
| 6,911,038 B2 | 6/2005 | Mertens et al. |
| 6,926,690 B2* | 8/2005 | Renati ........................... 604/8 |
| 2001/0008976 A1 | 7/2001 | Wang |
| 2001/0011188 A1 | 8/2001 | Berry et al. |
| 2001/0020181 A1 | 9/2001 | Layne |
| 2001/0023356 A1* | 9/2001 | Raz et al. .................... 606/191 |
| 2001/0037137 A1 | 11/2001 | Vardi et al. |
| 2001/0041930 A1* | 11/2001 | Globerman et al. ........ 623/1.16 |
| 2002/0058984 A1 | 5/2002 | Butaric et al. |
| 2002/0058993 A1* | 5/2002 | Landau et al. ............. 623/1.35 |
| 2002/0116047 A1* | 8/2002 | Vardi et al. ................ 623/1.11 |
| 2002/0156516 A1 | 10/2002 | Vardi et al. |
| 2002/0169498 A1* | 11/2002 | Kim et al. .................. 623/1.15 |
| 2002/0173840 A1 | 11/2002 | Brucker et al. |
| 2002/0183763 A1 | 12/2002 | Callol et al. |
| 2002/0183780 A1 | 12/2002 | Wang |
| 2002/0193862 A1 | 12/2002 | Mitelberg et al. |
| 2002/0193868 A1 | 12/2002 | Mitelberg et al. |
| 2002/0198559 A1* | 12/2002 | Mistry et al. ............... 606/194 |
| 2003/0083734 A1 | 5/2003 | Friedrich et al. |
| 2003/0097171 A1* | 5/2003 | Elliott ....................... 623/1.15 |
| 2003/0114912 A1* | 6/2003 | Sequin et al. .............. 623/1.11 |
| 2003/0125797 A1* | 7/2003 | Chobotov et al. .......... 623/1.13 |
| 2003/0199967 A1* | 10/2003 | Hartley et al. ............. 623/1.13 |
| 2004/0015227 A1 | 1/2004 | Vardi et al. |
| 2004/0024441 A1* | 2/2004 | Bertolino et al. ........... 623/1.12 |
| 2004/0054362 A1 | 3/2004 | Lopath et al. |
| 2004/0054396 A1* | 3/2004 | Hartley et al. ............. 623/1.13 |
| 2004/0073250 A1 | 4/2004 | Pederson, Jr. et al. |
| 2004/0093058 A1* | 5/2004 | Cottone et al. ............. 623/1.11 |
| 2004/0106985 A1 | 6/2004 | Jang |
| 2004/0133268 A1 | 7/2004 | Davidson et al. |
| 2004/0138730 A1* | 7/2004 | Mitelberg et al. ............ 623/1.2 |
| 2004/0138737 A1 | 7/2004 | Davidson et al. |
| 2004/0143209 A1 | 7/2004 | Liu et al. |
| 2004/0158306 A1 | 8/2004 | Mitelberg et al. |
| 2004/0204754 A1 | 10/2004 | Kaplan et al. |
| 2004/0220655 A1* | 11/2004 | Swanson et al. ........... 623/1.11 |
| 2004/0249434 A1 | 12/2004 | Andreas et al. |
| 2004/0254627 A1* | 12/2004 | Thompson et al. ......... 623/1.11 |
| 2004/0260378 A1 | 12/2004 | Goshgarian |
| 2004/0260383 A1 | 12/2004 | Stelter et al. |
| 2005/0010278 A1 | 1/2005 | Vardi et al. |
| 2005/0015108 A1 | 1/2005 | Williams et al. |
| 2005/0049678 A1* | 3/2005 | Cocks et al. ............... 623/1.15 |
| 2005/0154447 A1* | 7/2005 | Goshgarian ................ 623/1.15 |
| 2005/0165469 A1* | 7/2005 | Hogendijk ................. 623/1.15 |
| 2005/0192656 A1 | 9/2005 | Eidenschink |
| 2005/0203563 A9 | 9/2005 | Pederson, Jr. et al. |
| 2005/0209674 A1 | 9/2005 | Kutscher et al. |
| 2005/0228483 A1* | 10/2005 | Kaplan et al. .............. 623/1.15 |
| 2005/0234536 A1 | 10/2005 | Mitelberg et al. |
| 2005/0251195 A1 | 11/2005 | Wang |
| 2005/0261722 A1 | 11/2005 | Crocker et al. |
| 2005/0288769 A1* | 12/2005 | Globerman ................ 623/1.15 |
| 2006/0025849 A1* | 2/2006 | Kaplan et al. .............. 623/1.15 |
| 2006/0079952 A1* | 4/2006 | Kaplan et al. .............. 623/1.11 |
| 2006/0116748 A1* | 6/2006 | Kaplan et al. .............. 623/1.11 |
| 2007/0203571 A1 | 8/2007 | Kaplan et al. |
| 2007/0213803 A1 | 9/2007 | Kaplan et al. |
| 2007/0213804 A1 | 9/2007 | Kaplan et al. |
| 2007/0276460 A1 | 11/2007 | Davis et al. |
| 2008/0015610 A1 | 1/2008 | Kaplan et al. |
| 2008/0015678 A1 | 1/2008 | Kaplan et al. |
| 2008/0183269 A2 | 7/2008 | Kaplan et al. |

FOREIGN PATENT DOCUMENTS

| | | |
|---|---|---|
| EP | 0 959 811 B1 | 5/1997 |
| EP | 0876 805 A2 | 5/1998 |
| EP | 1 433 441 A2 | 11/1999 |
| EP | 1 325 715 A2 | 1/2003 |
| EP | 1 325 716 A1 | 1/2003 |
| EP | 1 325 717 A2 | 1/2003 |
| EP | 1 362 564 A1 | 5/2003 |
| WO | WO 96/38101 | 12/1996 |
| WO | WO 98/24503 | 6/1998 |
| WO | WO 00/69367 | 11/2000 |
| WO | WO 02/49538 A2 | 6/2002 |
| WO | WO 2004/026180 A2 | 4/2004 |
| WO | WO 2004/058100 A2 | 7/2004 |
| WO | WO 2004/089249 A1 | 10/2004 |
| WO | WO 2004/103217 A1 | 12/2004 |

OTHER PUBLICATIONS

Protection of Side-Branches in Coronary Lesions With a New Stent Design, Stephan Baldus, MD et al., *Catherization and Cardiovascular Diagnosis*, vol. 45: No. 4, 456-459, Dec. 1998.

Endovascular Grafts: History of Minimally Invasive Treatment of Vascular Disease, Timothy A.M. Chuter, *Endoluminal Vascular Prostheses*, pp. 3-17, 1995.

Self-expanding Stainless Steel Biliary Stents, Harold G. Coons, MD, *Radiology*, vol. 170, No. 3, Part 2, pp. 979-983.

A New Team to Fight Arterial Disease, *Building Innovation & Construction Technology*, No. 10, Dec. 1999, http://www.cmit.csiro.au/innovation/1999-12/arterial.htm.

The Zenith endoluminal stent-graft system: suprarenal fixation, safety features, modular components, tenestration and custom crafting, Michael M.D. Lawrence-Brown et al., *Vascular and Endovascular Surgical Techniques*, Fourth Edition, pp. 219-223, 2001.

*The Impact of Stent Design on Proximal Stent-graft Fixation in the Abdominal Aorta: an Experimental Study*, T. Resch et al., European Journal of Vascular and Endovascular Surgery, vol. 20, No. 2, pp. 190-195, Aug. 2000.

Esophageal Strictures: Treatment with a New Design of Modified Gianturco Stent, Ho. Young Song, M.D. et al., *Radiology*, vol. 184, No. 3, pp. 729-734 Sep. 1992.

U.S. Appl. No. 10/584,968, filed Jun. 30, 2006, our reference ANVIL.001BNP1.

U.S. Appl. No. Not Yet Assigned, filed Nov. 21, 2006, our reference ANVIL.001CP4.

PCT International Search Report No. PCT/US05/36987.

Supplementary European Search Report for Application No. EP 04759166.4 dated Mar. 5, 2007 in 4 pages (ANVIL.001VEP).

International Search Report and Written Opinion in PCT Application No. PCT/US04/10591dated Mar. 11, 2005 in 6 pages (ANVIL.001VPC).

U.S. Appl. No. 11/744,796, filed May 4, 2007, our reference ANVIL.001BNPC1.

U.S. Appl. No. 11/744,812, filed May 4, 2007, our reference ANVIL.001BNPC2.

U.S. Appl. No. 11/744,802, filed May 4, 2007, our reference ANVIL.001BNPC3.

European Patent Office Communication (first substantive examination report) in Application No. 04 759 166.4—1526 dated Apr. 30, 2007 in 3 pages (ANVIL.001VEP).

U.S. Appl. No. 11/781,201, filed Jul. 20, 2007, our reference ANVIL. 003DV1.

U.S. Appl. No. 11/781,164, filed Jul. 20, 2007, our reference ANVIL. 003DV2.

International Search Report and Written Opinion in PCT Application No. PCT/US07/85429 dated Jun. 2, 2008 in 10 pages (ANVIL. 001PPC).

* cited by examiner

STENT FOR PLACEMENT AT LUMINAL OS

CROSS-REFERENCES TO RELATED APPLICATIONS

This application claims the benefit of U.S. Provisional Application No. 60/463,075, filed on Apr. 14, 2003, the full disclosure of which is incorporated herein by reference.

BACKGROUND OF THE INVENTION

1. Field of the Invention

The present invention relates generally to medical devices and methods. More particularly, the present invention relates to the structure and deployment of a segmented stent at a luminal os at a branching point in the vasculature or elsewhere.

Maintaining the patency of body lumens is of interest in the treatment of a variety of diseases. Of particular interest in the to the present invention are the transluminal approaches to the treatment of body lumens. More particularly, the percutaneous treatment of atherosclerotic disease involving the coronary and peripheral arterial systems. Currently, percutaneous coronary interventions (PCI) involve a combination of balloon dilation along with the placement of an endovascular prosthesis commonly referred to as a stent. A major limitation of PCI/stent procedure is restenosis, i.e., the re-narrowing of a blockage after successful intervention typically occurring in the initial three to six months. The recent introduction of drug eluting stents (DES) has dramatically reduced the incidence of restenosis in coronary vascular applications and offers promise in peripheral stents, venous grafts, arterial and prosthetic grafts, as well as A-V fistulae. In addition to vascular applications, stents are being employed in treatment of other body lumens including the gastrointestinal systems (esophagus, large and small intestines, biliary system and pancreatic ducts) and the genital-urinary system (ureter, urethra, fallopian tubes, vas deferens).

While quite successful in treating arterial blockages and other conditions, most stent designs are challenged when used at a bifurcation in the blood vessel or other body lumen being treated. Presently, many different strategies are employed to treat bifurcation lesions with currently available stents all of which have major limitations.

One common approach is to place a conventional stent in the main or larger body lumen over the origin of the side branch. After removal of the stent delivery balloon, a second wire is introduced through a cell in the wall of the deployed stent and into the side branch. A balloon is then introduced into the side branch and inflated to enlarge the side-cell of the main vessel stent. This approach appears to work well when the side branch is relatively free of disease, although it is associated with increased rates of abrupt closure due to plaque shift as well as increased rates of late re-restenosis.

Another commonly employed strategy is the 'kissing balloon' technique in which separate balloons are positioned in the main and side branch vessels and simultaneously inflated. This technique is thought to prevent plaque shift.

Various two stent approaches including Culotte, T-Stent and Crush Stent techniques have been employed as well. When employing a T-stent approach, the operator deploys a stent in the side branch followed by placement of a main vessel stent. This approach is limited by anatomic variation (angle between main and side branch) and inaccuracy in stent positioning, which together can cause inadequate stent coverage of the os. More recently, the Crush approach has been introduced in which the side-vessel stent is deployed across the os with portions in both the main and side branch vessels. The main vessel stent is then delivered across the origin of the side branch and deployed, which results in crushing a portion of the side branch stent against the wall of the main vessel. Following main-vessel stent deployment, it is difficult and frequently not possible to re-enter the side branch after crush stenting. Unproven long-term results coupled with concern regarding the inability to re-enter the side branch and the impact of three layers of stent (which may be drug eluting) opposed against the main vessel wall has limited the adoption of this approach.

These limitations have led others to develop stents specifically designed to treat bifurcation lesions. One approach employs a stent design with a side opening for the branch vessel which is mounted on a specialized delivery balloon. The specialized balloon delivery system accommodates wires for both the main and side branch vessels. The system is tracked over both wires which provides a mean to axially and radially align the stent/stent delivery system. The specialized main vessel stent is then deployed and the stent delivery system removed while maintaining wire position in both the main and side branch vessels. The side branch is then addressed using kissing balloon or by delivering and an additional stent to the side branch. Though this approach has many theoretic advantages, it is limited by difficulties in tracking the delivery system over two wires (Vardi et al, U.S. Pat. Nos. 6,325,826 and 6,210,429).

For these reasons, it would be desirable to provide improved prostheses and methods for their placement to treat body lumens at or near the location of an os between a main body lumen and a side branch lumen, typically in the vasculature, and more particularly in the arterial vasculature. It would be further desirable if such prostheses and methods could treat the side branch vessels substantially completely in the region of the os and that the prostheses in the side branches be well-anchored at or near the os. At least some of these objectives will be met by the inventions described hereinbelow.

2. Description of the Background Art

Stent structures intended for treating bifurcated lesions are described in U.S. Pat. Nos. 6,599,316; 6,596,020; 6,325,826; and 6,210,429. Other stents and prostheses of interest are described in the following U.S. Pat. Nos. 4,994,071; 5,102, 417; 5,342,387; 5,507,769; 5,575,817; 5,607,444; 5,609,627; 5,613,980; 5,669,924; 5,669,932; 5,720,735; 5,741,325; 5,749,825; 5,755,734; 5,755,735; 5,824,052; 5,827,320; 5,855,598; 5,860,998; 5,868,777; 5,893,887; 5,897,588; 5,906,640; 5,906,641; 5,967,971; 6,017,363; 6,033,434; 6,033,435; 6,048,361; 6,051,020; 6,056,775; 6,090,133; 6,096,073; 6,099,497; 6,099,560; 6,129,738; 6,165,195; 6,221,080; 6,221,098; 6,254,593; 6,258,116; 6,264,682; 6,346,089; 6,361,544; 6,383,213; 6,387,120; 6,409,750; 6,428,567; 6,436,104; 6,436,134; 6,440,165; 6,482,211; 6,508,836; 6,579,312; and 6,582,394;

BRIEF SUMMARY OF THE INVENTION

The present invention provides improved prostheses and methods for their placement at an ostium (sometimes referred to herein as an os) opening from a main body lumen to a branch body lumen. The prostheses and methods will be principally useful in the vasculature, most typically the arterial vasculature, including coronary, peripheral, venous grafts, arterial and prosthetic grafts, as well as A-V fistulae. In addition to these vascular applications the present invention will also be useful in the treatment of other body lumens including the gastrointestinal systems (esophagus, large and small intestines, biliary system and pancreatic ducts) and the genital-urinary system (ureter, urethra, fallopian tubes, vas deferens), and the like.

The prostheses of the present invention are particularly advantageous since they permit substantially complete coverage of the wall of the branch body lumen up to the lumen os. Additionally, the prostheses have integrated anchoring components which expandably conform to and at least partially circumscribe the wall of the main body vessel to selectively and stably position the prosthesis within the side branch lumen. The anchoring components may be fully expanded to open the luminal passage through the main branch lumen. Such complete opening is an advantage since it provides patency through the main branch lumen. Moreover, the open main branch lumen permits optional placement of a second prosthesis within the main branch lumen using conventional techniques.

In a first aspect of the present invention, a prosthesis comprises a radially expansible scaffold and at least two "circumferential" anchors extending axially from an end of the scaffold. The anchors are adapted to "expandably circumscribe" a portion of, usually at least one-half of the circumference main vessel wall at or near the os when the scaffold is implanted in the branch lumen with one end of the scaffold adjacent the os. By "expandably circumscribe," it is meant that the anchors will extend into the main body lumen after initial placement of the scaffold within the branch body lumen. The circumferential anchors will be adapted to then be partially or fully radially expanded, typically by expansion of a balloon or other expandable element therein, so that the anchors deform outwardly and engage the interior of the main lumen wall.

The circumferential anchors will usually extend axially within the main vessel lumen for some distance after complete deployment. Thus, the contact between the anchors and the main vessel wall will usually extend both circumferentially (typically covering an arc equal to one-half or more of the circumference) and axially.

Expansion of the circumferential anchors at least partially within the main body lumen provides a generally continuous coverage of the os from the side body lumen to the main body lumen. Further and/or complete expansion of the circumferential anchors within the main body lumen may press the anchors firmly against the main body lumen wall and open up the anchors so that they do not obstruct flow through the main body lumen.

Usually, the prosthesis will include at least three circumferential anchors extending axially from the end of the scaffold. The prosthesis could include four, five, or even a greater number of circumferential anchors, but the use of three such anchors is presently preferred since a greater number could interfere with subsequent access by the second expansion balloon. The circumferential anchors will have an initial length (i.e., prior to radial expansion of the scaffold) which is at least 1.5 times the width of the scaffold prior to expansion, typically being at least 2 times the width, more typically being at least 5 times the width, and often being 7 times the width or greater. The lengths will typically be at least 2 mm, preferably being at least 3 mm, and more preferably being at least 6 mm, depending on the diameter of the scaffold and prosthesis. The circumferential anchors will usually have a width which is expandable to accommodate the expansion of the scaffold, and the anchors may be "hinged" at their point of connection to the scaffold to permit freedom to adapt to the geometry of the main vessel lumen as the prosthesis is expanded. It is also possible that the anchors could be attached to the single point to the scaffold, thus reducing the need for such expandability.

The anchors may be congruent, i.e., have identical geometries and dimensions, or may have different geometries and/or dimensions. In particular, in some instances, it may be desirable to provide anchors having different lengths and/or different widths.

Often, radiopaque or other visible markers will be placed on the prostheses and/or delivery balloon at desired locations. In particular, it may be desirable to provide radiopaque markers at or near the location on the prosthesis where the scaffold is joined to the circumferential anchors. Such markers will allow a transition region of the prosthesis between the scaffold and the anchors to be properly located near the os prior to scaffold expansion. Note that it is also possible to provide the radiopaque or other markers on a balloon or other delivery catheter, where the markers would also be aligned with the transition region between the scaffold and the circumferential anchors.

In a second aspect of the present invention, a prosthesis is deployed across an os opening from the main body lumen to a branch body lumen. The prosthesis is positioned so that a scaffold of the prosthesis lies within the branch body lumen and at least two, typically at least three, circumferential anchors extend from the scaffold at the os into the main body lumen. The scaffold is radially expanded to implant the scaffold in the branch body lumen. While at least some of the anchors may initially obstruct the lumen, the anchors are subsequently circumferentially deformed (usually after expansion of the scaffold) to circumscribe at least a portion of the main vessel wall, with at lest one anchor typically covering at least 50% of the circumferential length, preferably at least 60% of the circumferential length and often at least 75% or greater. In this way, the circumferential anchors will open a passage through the anchors and the main body lumen to permit generally unobstructed blood flow or flow of other body fluids. Positioning of the prosthesis will usually comprise aligning a visible marker on at least one of the prosthesis and delivery balloon with the os so that the prosthesis is properly positioned relative to both the side branch lumen and the main body lumen.

In an exemplary deployment protocol, the scaffold is first expanded with a balloon catheter positioned within the scaffold. The balloon catheter expands the scaffold within the branch body lumen and usually begins separating and deploying the circumferential anchors within the main body lumen. After the scaffold has been deployed, the anchors are deformed to circumscribe the wall of the main body lumen, typically using a balloon positioned transversely through the anchors. In some instances, the scaffold and the circumferential anchors may be expanded and deformed using the same balloon, e.g., the balloon is first used to expand the anchor, partially withdrawn, and advanced traversely through the circumferential anchors where it is expanded for a second time. Alternatively, separate balloon catheters may be employed for expanding scaffold within the side branch and deforming the circumferential anchors within the main body lumen.

Optionally, a second prosthesis may be deployed within the passage formed through the circumferential anchors. For example, the second prosthesis may be deployed by a balloon catheter exchanged over a guidewire pre-positioned for deformation of the anchors. Alternatively, although less preferable, the anchors may be deformed by deployment of the second prosthesis in order to reduce the procedure by one step.

DETAILED DESCRIPTION OF THE INVENTION

Figure 1:
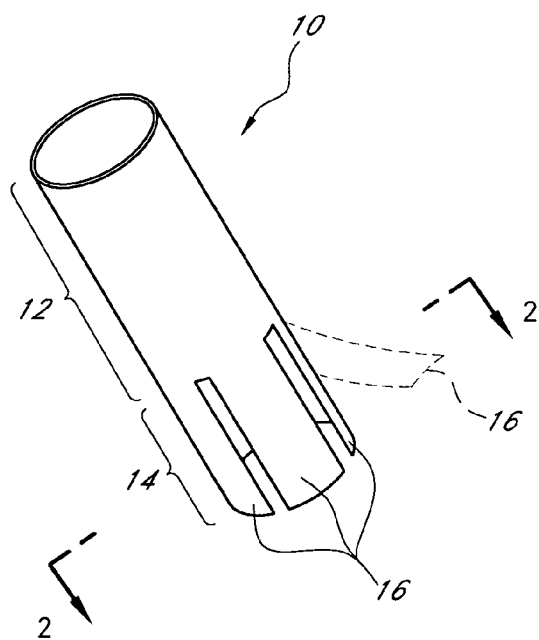
FIG. 1 is a schematic illustration of a prosthesis constructed in accordance with the principles of the present invention.
Figure 2:
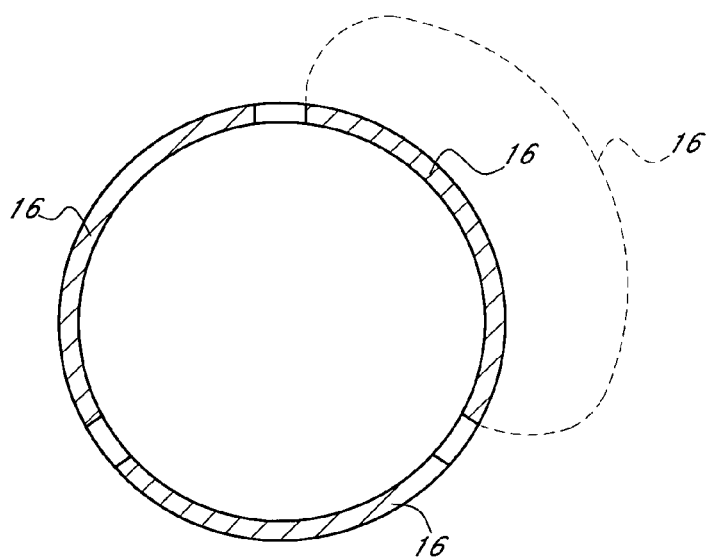
FIG. 2 is a cross-sectional view taken along line 2-2 of FIG. 1.

Referring to FIGS. 1 and 2, a stent 10 constructed in accordance with the principles of the present invention includes at least a radially expansible scaffold section 12 and an anchor section 14. The anchor section 14 includes at least two axially aligned circumferential anchors 16, with three being illustrated. The radially expansible scaffold section 12 will typically be balloon expandable and may be formed using a variety of conventional patterns and fabrication techniques as are well-described in the prior art. Many particular patterns and fabrication techniques are described in the patents which are listed in the Background section above, and the teachings of those patents are hereby incorporated by reference herein in their entirety.

The circumferential anchors 16 will usually extend axially from the scaffold section 12, as illustrated, but in some circumstances the anchors could extend helically, spirally, in a serpentine pattern, or other configurations. It is necessary, however, that the individual circumferential anchors be radially separable so that they can be independently folded, bent, and otherwise positioned within the main body lumen after the scaffold section 12 has been implanted within the branch body lumen. In the schematic embodiment of FIG. 1A, the circumferential anchors 16 may be independently folded out in a "petal-like" configuration, as generally shown in broken line for one of the anchors in FIGS. 1 and 2.

Figure 1A:
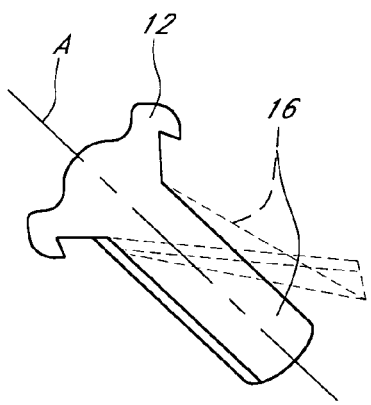
FIG. 1A is a detailed view of an anchor of the prosthesis of FIG. 1, shown with the anchor deployed in broken line.

In preferred embodiments, the circumferential anchors 16 will be attached to the scaffold section 12 such that they can both bend and rotate relative to an axis A thereof, as shown in broken line in FIG. 1A. Bending will occur radially outwardly and rotation or twisting can occur about the axis A as the anchor is bent outwardly. Such freedom of motion can be provided by single point attachment joints as well as the three-point attachments shown in FIG. 3. Moreover, the expandable and bendable nature of anchors 62 in FIG. 3 will also permit both radially outward bending and twisting and rotation to help the anchors conform to the inside of the main vessel lumen in which they are deployed.

Figure 3:
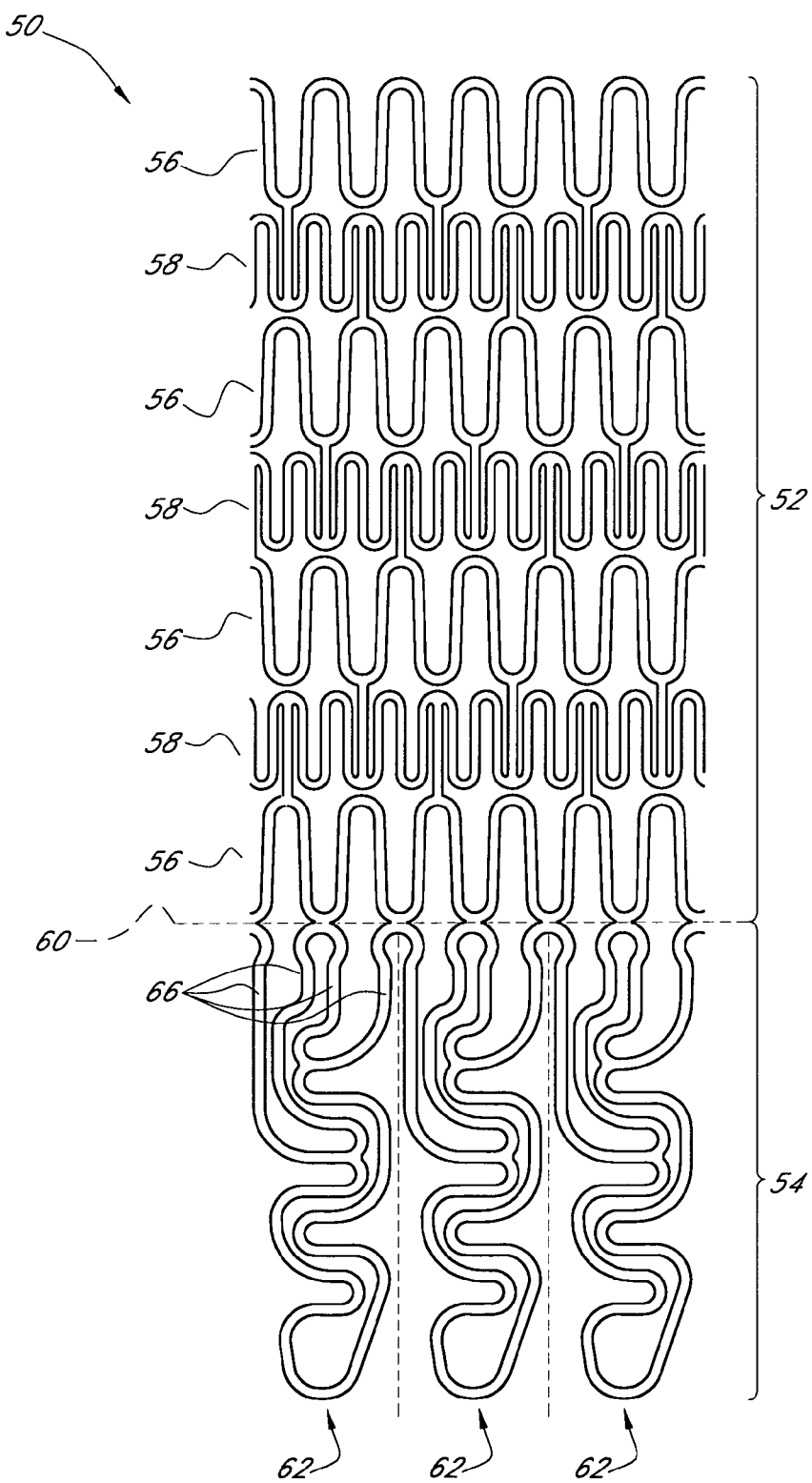
FIG. 3 is a "rolled-out" illustration of an exemplary prosthesis constructed in accordance with the principles of the present invention.

Referring now to FIG. 3, an exemplary prosthesis structure 50 (shown in a "rolled out" pattern) comprises a scaffold section 52 and a circumferential anchor section 54. Scaffold section 52 comprises a plurality of radially expansible serpentine cells 56 joined by smaller cells 58 comprising beams and a serpentine ring. The particular pattern illustrated for this structure is well-known and chosen to be exemplary of a useful scaffold. It will be appreciated that a wide variety of other conventional stent structures and patterns would be equally useful as the scaffold section of the prostheses of the present invention.

The scaffold section 52 is joined to the circumferential anchor section 54 at a plurality of points along a transition line 60. Individual circumferential anchors 62 each comprise four curving elements 66 which reduce in number to three and then to two in the axial direction away from the transition region 60. The particular structures shown permit radial expansion of the individual anchors as the scaffold is expanded. This is necessary since each circumferential anchor 62 is attached to three adjacent serpentine ring elements in the final serpentine ring 56. Thus, as these serpentine rings 56 are expanded, the circumferential anchor structures will also expand. It would be possible, of course, to join each of the circumferential anchors 62 only at a single location to the scaffold 52, thus allowing the anchors to be deployed without radial expansion.

The circumferential anchors 62 are curved and have a number of hinge regions which increase their conformability upon circumferential expansion by a balloon, as described hereinafter. Such conformability is highly desirable since the anchors will be expanded under a wide variety of differing conditions which will result in different final geometries for the anchors in use. The final configuration of the anchors in the main vessel lumen will depend on a number of factors, including length of the anchors and geometry of the vasculature and will vary greatly from deployment to deployment. While the anchors together will cover at least a portion of the main vessel wall circumference, most anchors will also be deformed to cover a significant axial length of the main vessel wall as well. Such coverage is schematically illustrated in the figures discussed below.

Figure 4A:
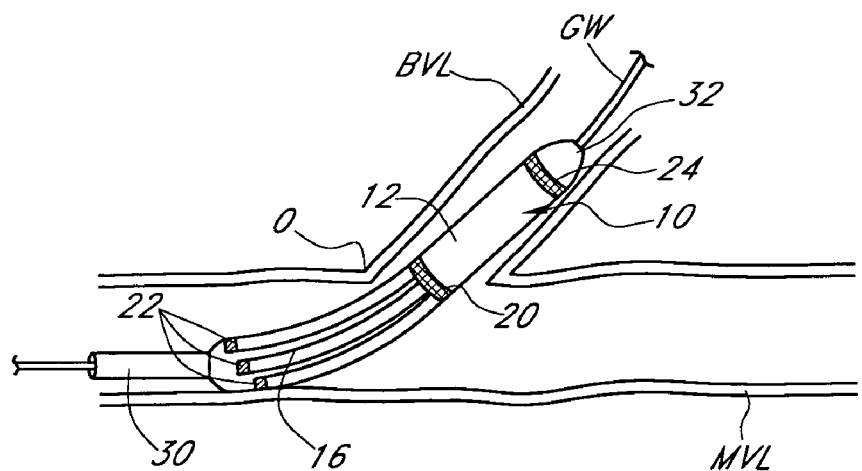
FIGS. 4A-9B illustrate deployment of a stent at an os between a main blood vessel and a side branch blood vessel in accordance with the principles of the methods of the present invention.

Referring now to FIGS. 4A-9B, deployment of the stent 10 in accordance with the principles of the present invention will be described. A stent 10 is carried to an os O located between a main vessel lumen MVL and a branch vessel lumen BVL in the vasculature, as shown in FIGS. 4A and 4B. Usually, the stent 10 will include at least one radiopaque marker 20 on stent 10 located near the transition region between the scaffold section 12 and the circumferential anchors 16. The radiopaque marker 20 can be aligned with the os O, typically under fluoroscopic imaging. Optionally, the stent 10 may include additional radiopaque markers, such as markers 22 and 24 at the ends of and/or elsewhere on the stent. The stent 10 is delivered by a balloon catheter 30 which may be introduced over a single guidewire GW which passes from the main vessel lumen MVL through the os O into the branch vessel BVL. Optionally, a second guidewire (not shown) which passes by the os O in the main vessel lumen MVL may also be employed.

Figure 4B:
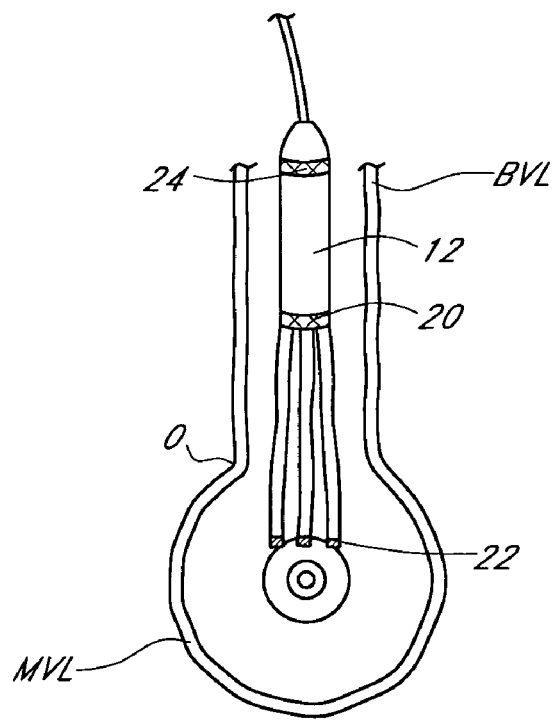
Figures 5A, 5B:
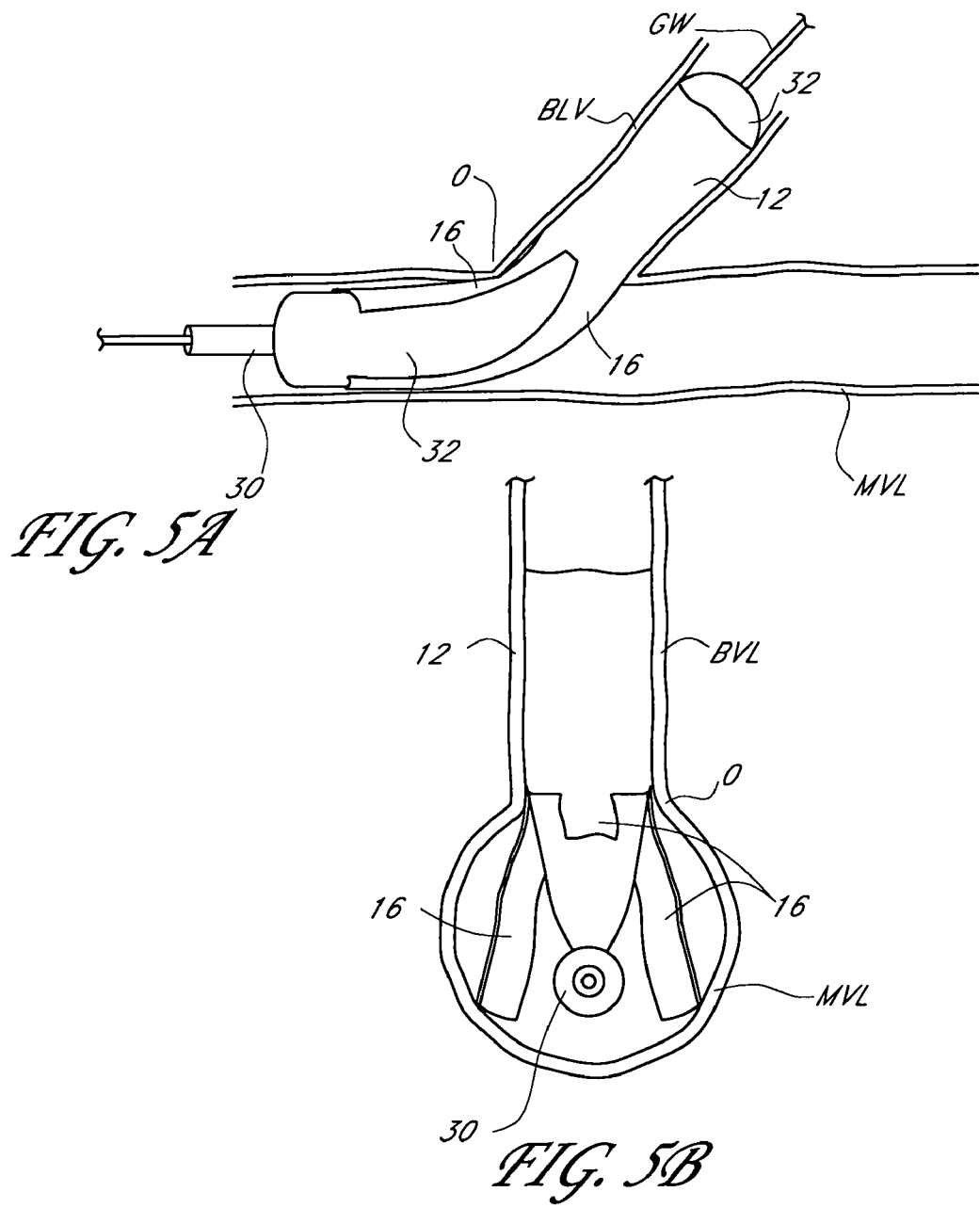

After catheter 30 is positioned so that the marker 20 is adjacent the os O, as shown in FIGS. 4A and 4B, a balloon 32 which carries the stent is expanded to implant the scaffold region 10 within the branch vessel lumen BVL, as shown in FIGS. 5A and 5B. Expansion of the balloon 30 also partially deploys the circumferential anchors 16, opening them in a petal-like manner, as shown in FIG. 5B, typically extending both circumferentially and axially into the main vessel lumen MVL. The anchors 16, however, are not fully deployed and may remain at least partially within the central region of the main vessel lumen MVL.

Figure 6A:
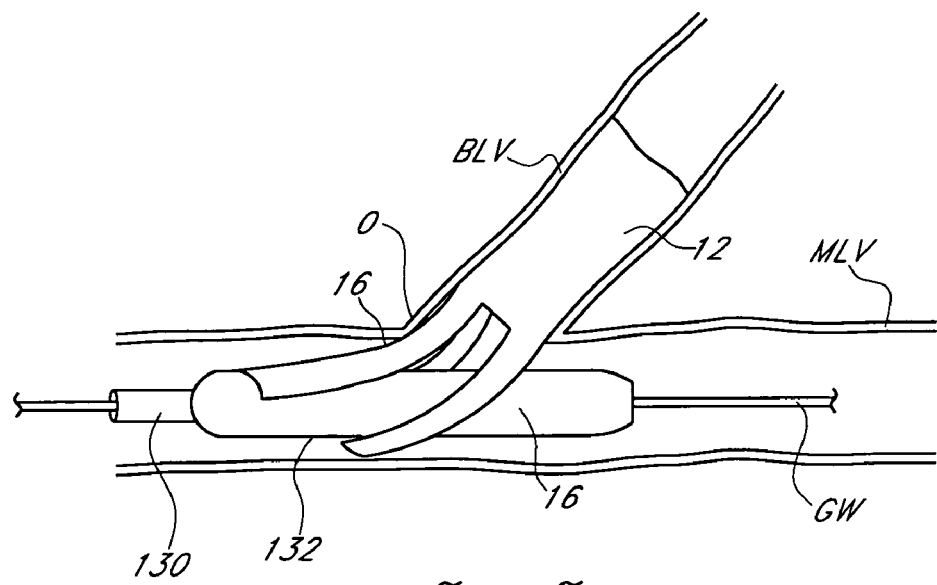
Figure 6B:
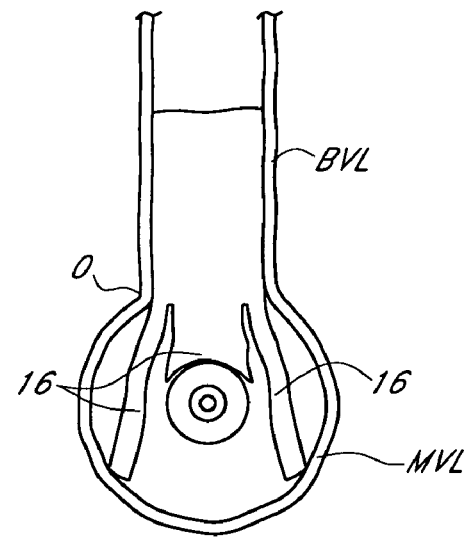

In order to fully open the anchors 16, a second balloon catheter 130 is introduced over a guidewire GW to position the balloon 132 within the anchors, as shown in FIGS. 6A and 6B. Optionally, the first catheter 30 could be re-deployed, for example by partially withdrawing the catheter, repositioning the guidewire GW, and then advancing the deflated balloon 32 within the anchors 16. As it is generally difficult to completely deflate the balloon, however, and a partially inflated balloon would be difficult to pass through the anchors 16, it will generally be preferable to use the second balloon catheter 130 for the deforming the anchors 16. When using the second balloon catheter 130, a second GW will usually be prepositioned in the main vessel lumen MVL past the os 0, as shown in FIGS. 6A and 6B.

Figure 7A:
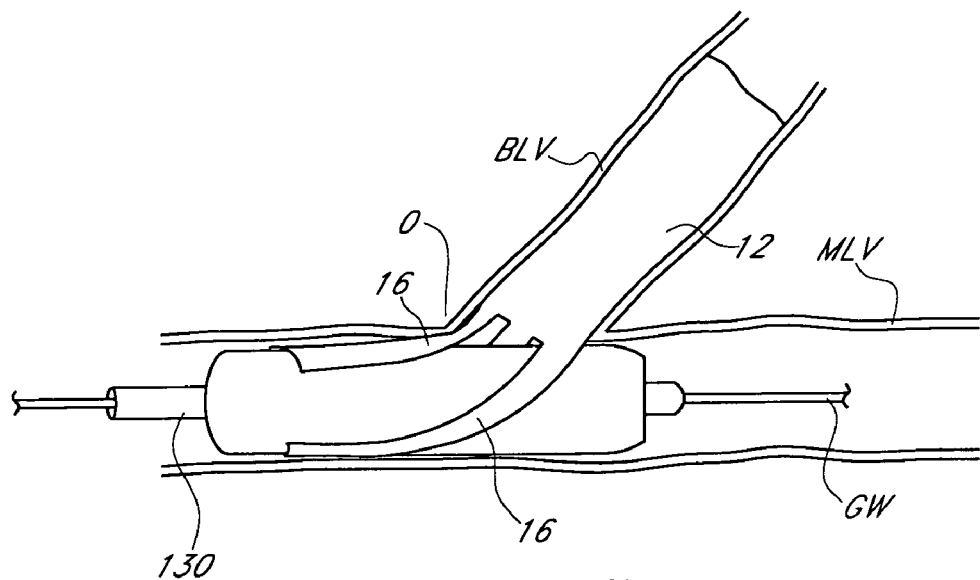
Figure 7B:
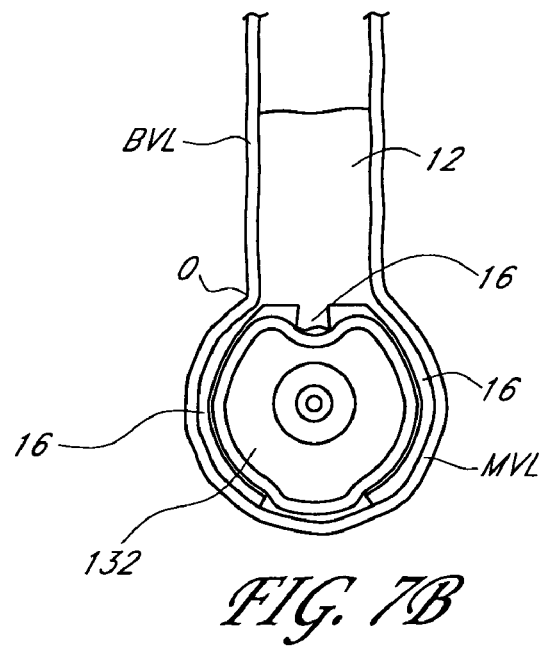
Figure 8A:
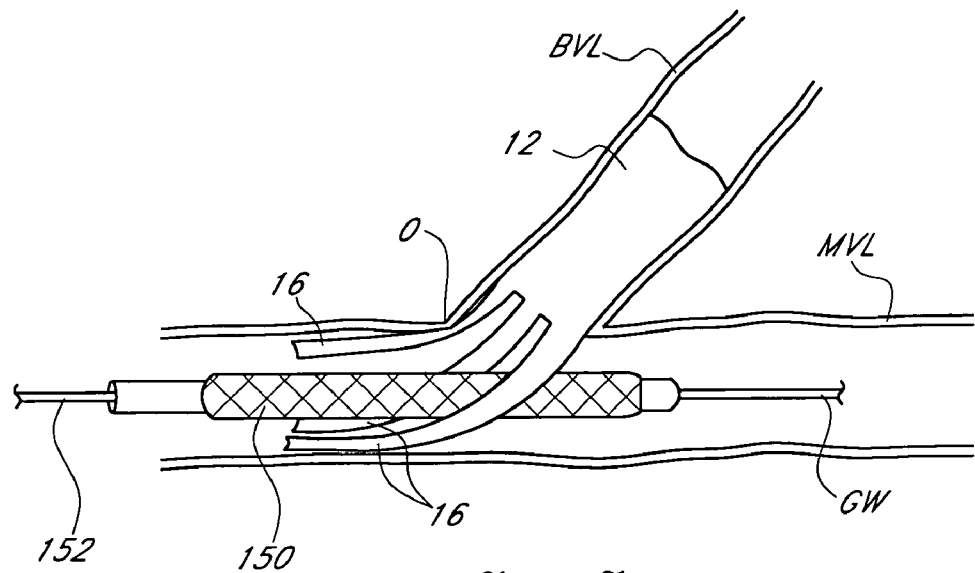
Figure 8B:
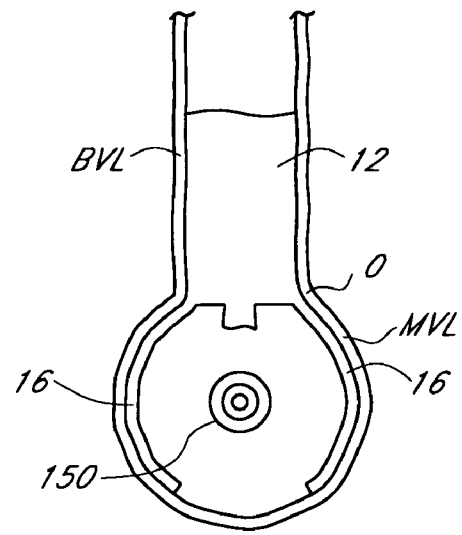
Figure 9A:
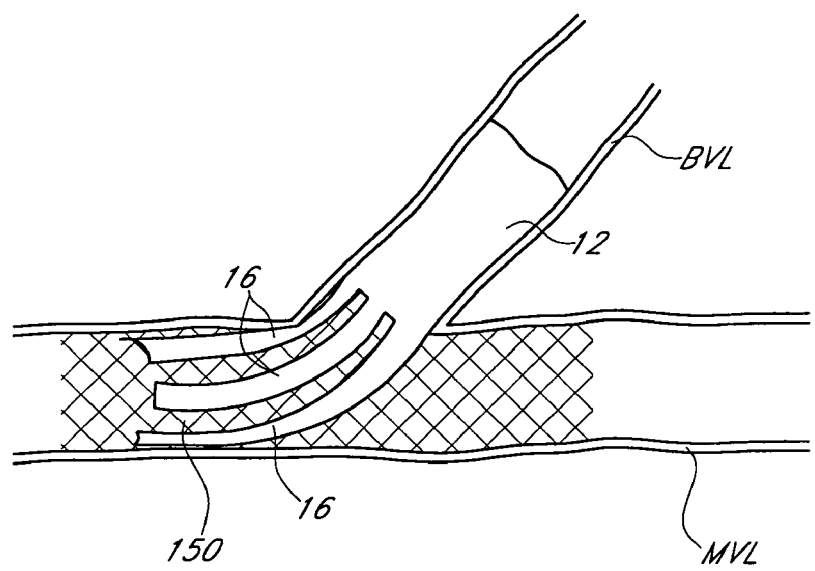
Figure 9B:
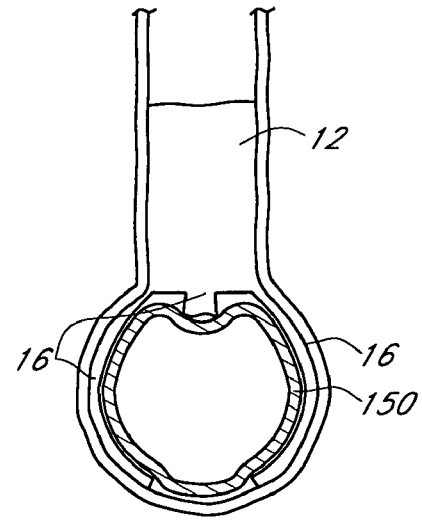

The anchors 16 are deformed by inflation of the balloon 132 within the anchors 16, as shown in FIGS. 7A and 7B. At this point, the protocol may be completed by withdrawing the second catheter 130, leaving the fully opened and deployed anchors 16 within the main vessel lumen MVL. Usually, however, it will be desirable to place a second stent or other prosthesis 150 within the deformed and deployed circumferential anchors 16 within the main vessel lumen MVL, as shown in FIGS. 8A, 8B, 9A and 9B. Catheter 152 is placed over the guidewire GW, typically the same guidewire used to deploy the second catheter 130, to position the stern 150 within the circumferential anchors 16 adjacent the os O (FIGS. 8A and 8B). The balloon of the catheter 152 is then inflated to deploy the second stent, as shown in FIGS. 9A and 9B. Optionally, another balloon catheter may be used open a passage through the stent 150 into the scaffold within the branch vessel lumen BVL.

When a second stent or prosthesis is deployed within the expanded anchor structure of the first prosthesis, the combination of the anchors and second stent both contribute to the support of the main vessel and os. In particular, the anchors are supported by the scaffold in the region of the os and over their lengths and tips by the deployed second stent.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A prosthesis for placement at an ostium opening from a main body lumen to a branch body lumen; the main body lumen having a main vessel wall with a portion of the main vessel wall opposing the ostium, said prosthesis comprising: a radially expansible scaffold having at least a first wall pattern; and at least two circumferential anchors extending axially from an end of the scaffold, said anchors having sufficient length to extend into and bend and rotate and thereby expandably circumscribe the main vessel wall and reach the portion of the main vessel wall opposing the ostium when the scaffold is implanted in the branch lumen with said one end adjacent the ostium, said prosthesis additionally having a region with a second wall pattern that is different from the first wall pattern, said second wall pattern permitting the anchors to both bend and rotate relative to the prosthesis, such that a flow path is maintained in the main body lumen between the anchors and beyond the ostium opening.

2. The prosthesis of claim 1, comprising at least three circumferential anchors extending axially from the end of the scaffold.

3. The prosthesis of claim 1, wherein the scaffold comprises a plurality of axially adjacent cells.

4. The prosthesis of claim 1, wherein the circumferential anchors are all congruent.

5. The prosthesis of claim 1, wherein the circumferential anchors will radially expand when the scaffold is radially expanded.

6. The prosthesis of claim 1, further comprising a radiopaque marker at or near the region with the second wall pattern.

7. The prosthesis of claim 1, mounted on a balloon wherein the balloon has a radiopaque marker aligned with the region between the scaffold and the circumferential anchors.

8. The prosthesis of claim 1, mounted on a balloon catheter.

9. The prosthesis of claim 1, comprising at least five anchors.

10. A method for deploying a prosthesis across an ostium opening from a main lumen to a branch lumen, the main body lumen having a main vessel wall with a portion of the main vessel wall opposing the ostium, said method comprising: positioning a first prosthesis so that a scaffold lies within the branch lumen and at least two circumferential anchors extend from the scaffold and into the main lumen; radially expanding the scaffold to implant said scaffold in the branch lumen; circumferentially deforming the anchors such that at least one of said anchors bends and rotates relative to the prosthesis, and has sufficient length to reach the portion of the main vessel wall opposing the ostium, said deforming causing the anchors to circumscribe at least a portion of the main lumen wall and open a passage between the anchors; and deploying a second prosthesis within the passage between the anchors, and wherein the anchors have an axial length which is at least 1.5 times the width of the scaffold prior to radial expansion.

11. The method of claim 10, wherein at least three circumferential anchors extend into the main lumen.

12. The method of claim 10, wherein positioning the first prosthesis comprises aligning a visible marker on at least one of the prosthesis and a delivery balloon with the ostium.

13. The method of claim 10, wherein the lumens are blood vessels.

14. The method of claim 10, wherein the scaffold is expanded with a balloon expanded within the scaffold.

15. The method of claim 14, wherein the anchors are deformed by expanding a balloon positioned transversely between the anchors.

16. The method of claim 15, wherein the scaffold and anchors are expanded and deformed by the same balloon.

17. The method of claim 15, wherein the scaffold and anchors are expanded and deformed by different balloons.

18. The method of claim 10, wherein the second prosthesis is deployed by a balloon catheter exchanged over a guidewire pre-positioned for deformation of the anchors.

19. The method of claim 10, wherein the anchors are deformed by deployment of the second prosthesis.

20. The method of claim 10, wherein the deployed second prosthesis supports the anchors over their lengths from the ostium along the main lumen wall.

21. A prosthesis for placement at an ostium opening from a main body lumen to a branch body lumen, the main body lumen having a main vessel wall with a portion of the main vessel wall opposing the ostium, said prosthesis comprising: a one piece body including a radially expansible scaffold having at least a first wall pattern; and at least one anchor extending from an end of the scaffold, said anchor having a length sufficient to circumscribe the main vessel wall and reach the portion of the main vessel wall opposing the ostium when the scaffold is implanted in the branch lumen with said one end adjacent the ostium, and wherein the anchor is configured to bend and rotate thereby enabling it to circumscribe the main vessel wall, said prosthesis additionally having a region with a second wall pattern that is different from the first wall pattern, said second wall pattern permitting the anchors to both bend and rotate relative to the prosthesis, such that a flow path is maintained in the body lumen between the anchors and beyond the ostium opening.

22. The prosthesis of claim 21, wherein the anchor extends helically from the scaffold.

23. The prosthesis of claim 22, additionally comprising a radiopaque marker.

24. The prosthesis of claim 22, mounted on a balloon catheter.

25. The prosthesis of claim 21, comprising at least three anchors.

26. The prosthesis of claim 21, comprising at least five anchors.

27. The prosthesis of claim 21, additionally comprising a radiopaque marker.

28. The prosthesis of claim 21, mounted on a balloon catheter.

29. A method for deploying a prosthesis across an ostium opening from a main lumen to a branch lumen, the main body lumen having a main vessel wall with a portion of the main vessel wall opposing the ostium, said method comprising: providing a first prosthesis having a scaffold and at least two anchors; positioning the first prosthesis so that the scaffold lies within the branch lumen and the at least two anchors extend into the main lumen; radially expanding the scaffold to implant said scaffold in the branch lumen; bending and rotating at least one anchor such that it extends circumferentially along the main vessel wall a sufficient distance to reach the portion of the main vessel wall opposing the ostium.

* * * * *

UNITED STATES PATENT AND TRADEMARK OFFICE
CERTIFICATE OF CORRECTION

PATENT NO. : 7,481,834 B2  
APPLICATION NO. : 10/807643  
DATED : January 27, 2009  
INVENTOR(S) : Aaron V. Kaplan Page 1 of 1

It is certified that error appears in the above-identified patent and that said Letters Patent is hereby corrected as shown below:

In column 3, line 1, delete "duets)" insert --ducts--.
In column 7, line 20, delete "stern" insert --stent--.

Signed and Sealed this

Second Day of June, 2009

JOHN DOLL
*Acting Director of the United States Patent and Trademark Office*